United States Patent [19]

Stobie et al.

[11] Patent Number: 5,604,976
[45] Date of Patent: Feb. 25, 1997

[54] METHOD OF MAKING PERCUTANEOUS CONNECTOR FOR MULTI-CONDUCTOR ELECTRICAL CABLES

[75] Inventors: John J. Stobie, Portland, Oreg.; Edward M. Schmidt, Bethesda; Martin J. Bak, Germantown, both of Md.; Scott S. Corbett, III, Portland, Oreg.; Thomas R. Clary, Issaquah, Wash.; David Edell, Lexington, Mass.; Fredrick T. Hambrecht, Rockville, Md.; William J. Heetderks, Silver Spring, Md.; Conrad V. Kufta, Rockville, Md.

[73] Assignees: PI Medical Corporation, Portland, Oreg.; The United States of America as represented by the Department of Health and Human Services, Washington, D.C.

[21] Appl. No.: 326,291

[22] Filed: Oct. 18, 1994

[51] Int. Cl.⁶ .................................................. H01R 43/02
[52] U.S. Cl. ............................... 29/825; 29/860; 264/263
[58] Field of Search ...................... 29/860, 825; 264/263, 264/272.15

[56] References Cited

U.S. PATENT DOCUMENTS

| Re. 33,170 | 2/1990 | Byers | 128/419 |
|---|---|---|---|
| 3,409,864 | 11/1968 | Hoffman | 264/272.11 X |
| 3,447,161 | 6/1969 | Weikel | 3/1 |
| 3,924,916 | 12/1975 | Venaleck | 339/17 |
| 3,995,644 | 12/1976 | Parsons | 128/418 |
| 4,025,964 | 5/1977 | Owens | 3/1 |
| 4,209,481 | 6/1980 | Kashiro et al. | 264/272.11 X |
| 4,434,134 | 2/1984 | Darrow et al. | 419/5 |
| 4,645,504 | 2/1987 | Byers | 623/10 |
| 4,686,765 | 8/1987 | Byers et al. | 29/858 |
| 4,819,647 | 4/1989 | Byers et al. | 128/642 |
| 4,875,870 | 10/1989 | Hardy et al. | 439/204 |
| 5,026,397 | 6/1991 | Aoki et al. | 623/11 |
| 5,035,711 | 7/1991 | Aoki et al. | 623/11 |
| 5,274,917 | 1/1994 | Corbett, III et al. | 29/860 |

FOREIGN PATENT DOCUMENTS

| 1-97382 | 4/1989 | Japan | 264/272.11 |

OTHER PUBLICATIONS

Klomp et al., "Percutaneous Connections in Man," Transactions, American Society for Artificial Organs, vol. XXV, 1979.

West et al., "In Vivo Bone-Bonding Study of Bioglass®-Coated Titanium Alloy," CRC Handbook of Bioactive Ceramics, vol. 1, pp. 161-166, earlier than Oct. 18, 1993.

Poole-Warren et al., "In Vivo Response to Ceramic Percutaneous Implants," Bioceramics, vol. 4, pp. 187-190, 1991.

(List continued on next page.)

*Primary Examiner*—Carl J. Arbes
*Attorney, Agent, or Firm*—Chernoff, Vilhauer, McClung & Stenzel

[57] ABSTRACT

A biologically implantable percutaneous connector for providing optionally separable interconnection of a large number of small electrical conductors of an externally located electrical cable includes a mating face incorporating an array of exposed end surfaces of tiny conductive rods sealed in a supporting matrix of dielectric material which is supported in a connector body. Elastomeric anisotropic connector material is located between corresponding arrays of contacts to provide for repeated reliable electrical connection and disconnection. External surfaces of the implantable body of the percutaneous connector are coated with a bioactive material promoting integration of surrounding tissue into the surfaces of the implanted percutaneous connector. A contact block including the mating face and a terminal face to which the conductors of a cable are individually connected is made by shaping an array of conductive rods and supporting dielectric material to form a smooth surface including dielectric matrix material and the ends of the electrically conductive rods.

34 Claims, 10 Drawing Sheets

OTHER PUBLICATIONS

Yoshiyama et al., "Hydroxylapatite Percutaneous Access Device in Peritoneal Dialysis," CRC Handbook of Bioactive Ceramics, vol. II, pp. 377–385, earlier than Oct. 18, 1993.

Tsuji et al., "Implantation in the Human Forearm of a Percutaneous Device Made of Sintered Hydroxylapatite," CRC Handbook of Bioactive Ceramics, vol. II, pp. 373–376, earlier than Oct. 18, 1993.

Chehroudi et al., "The role of connective tissue in inhibiting epithelial downgrowth on titanium–coated percutaneous implants," 1992.

Jansen et al., "Tissue response to percutaneous implants in rabbits," Journal of Biomedical Materials Research, vol. 24, pp. 295–307, 1990.

Akazawa et al., "Functional Neuromuscular Stimulation System Using an Implantable Hydroxyapatite Connector and a Microprocessor–Based Portable Stimulator," IEEE Transactions of Biomedical Engineering, vol. 36, No. 7, 1989.

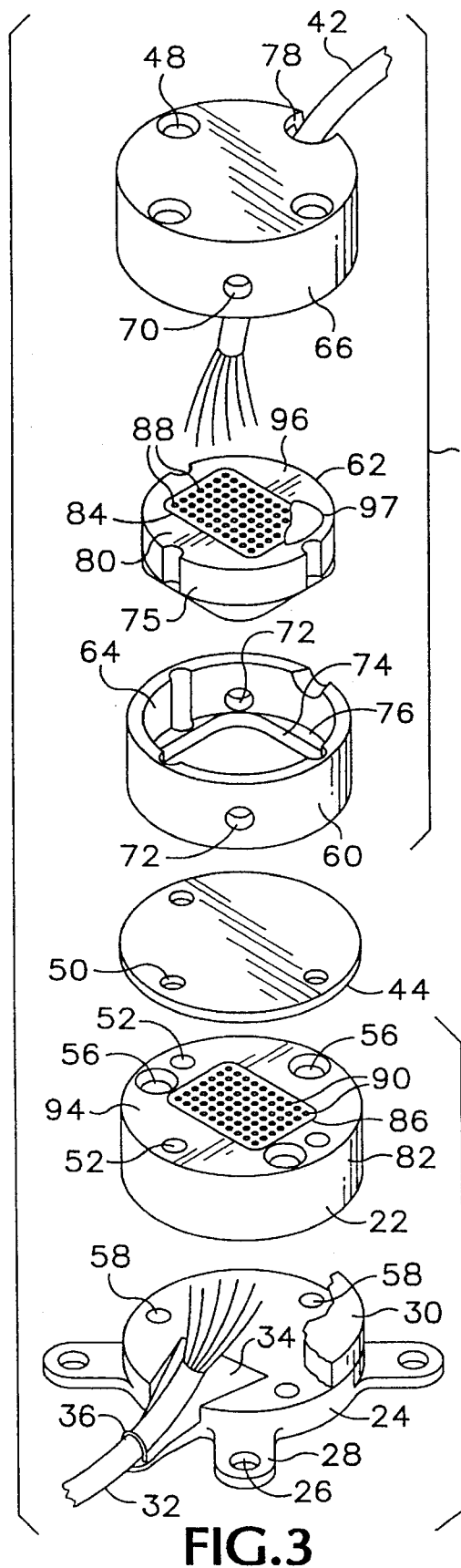

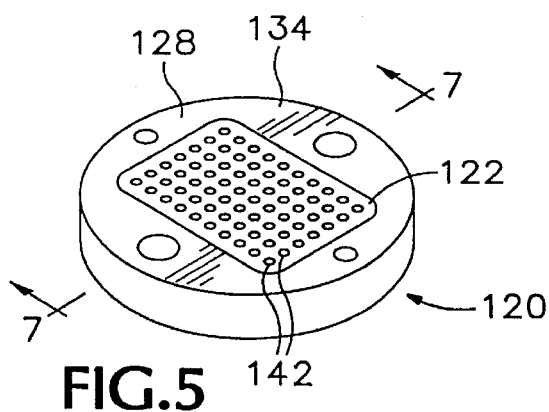
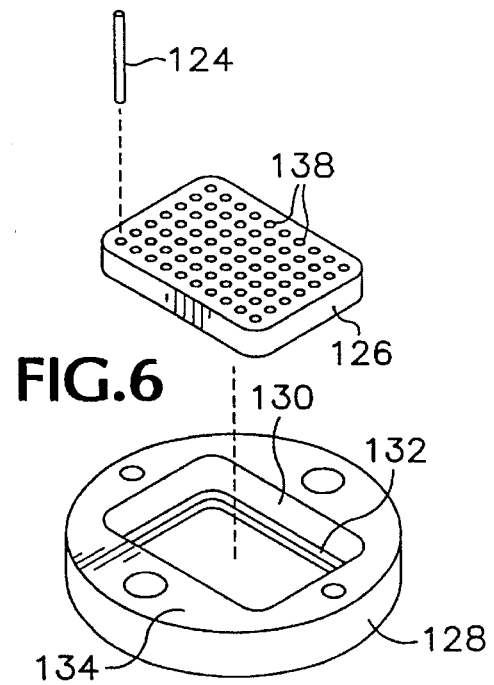
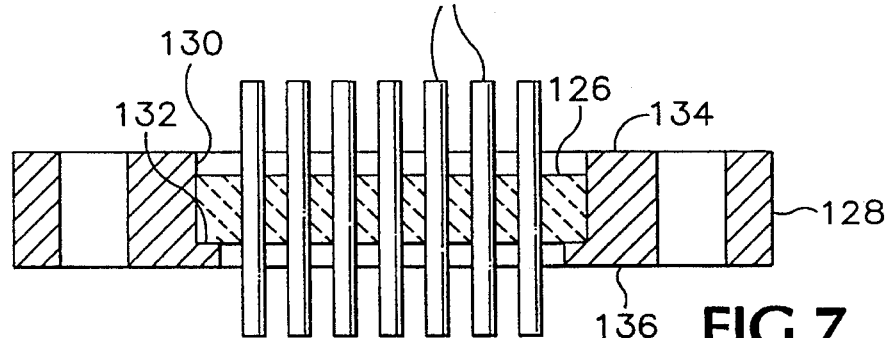
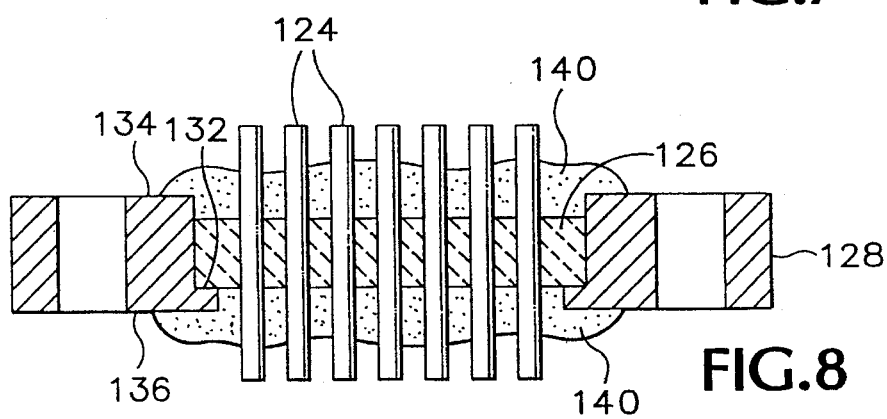
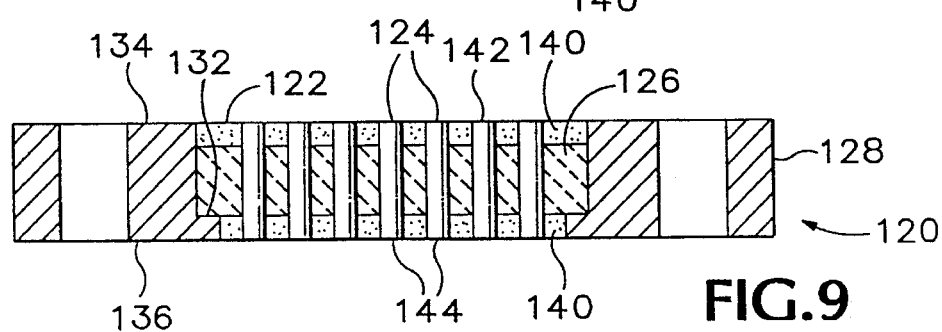

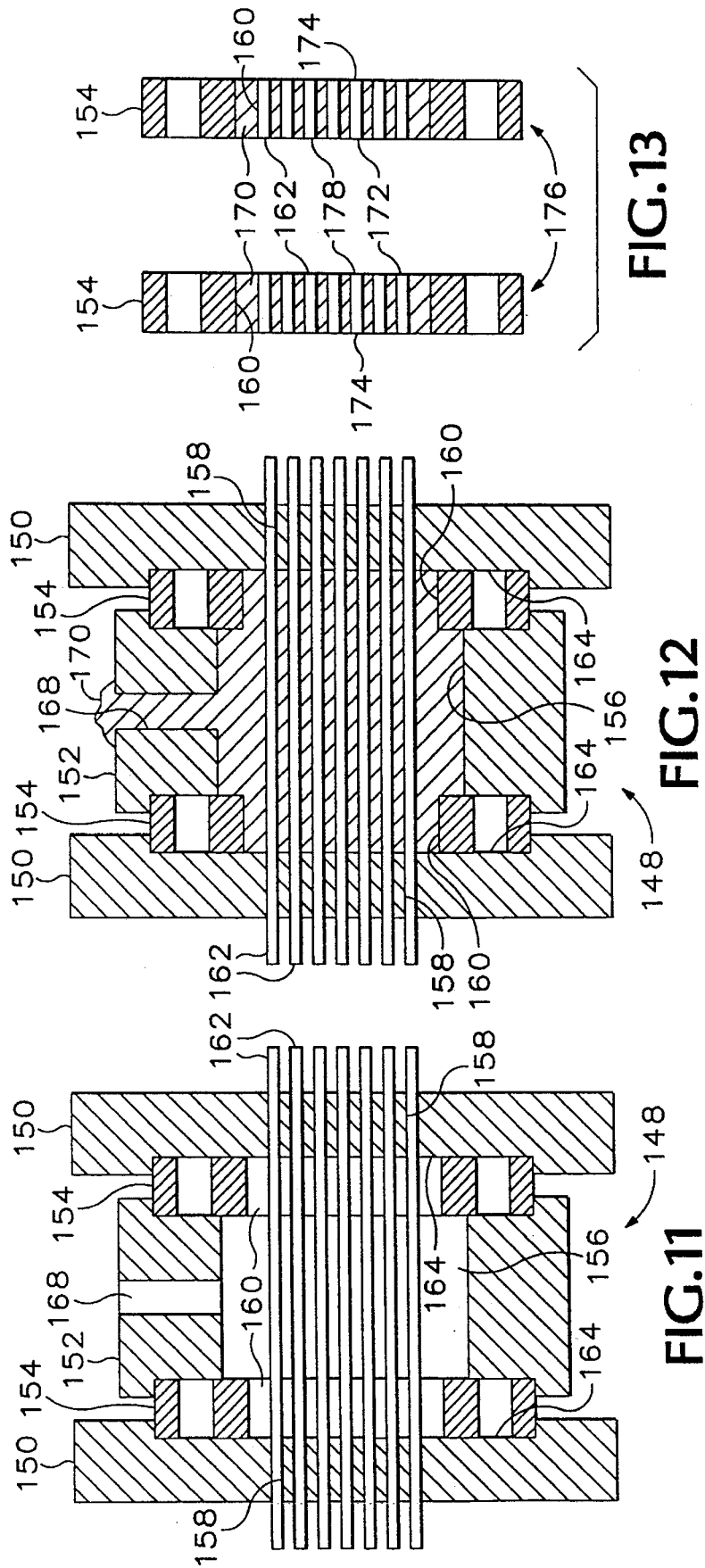

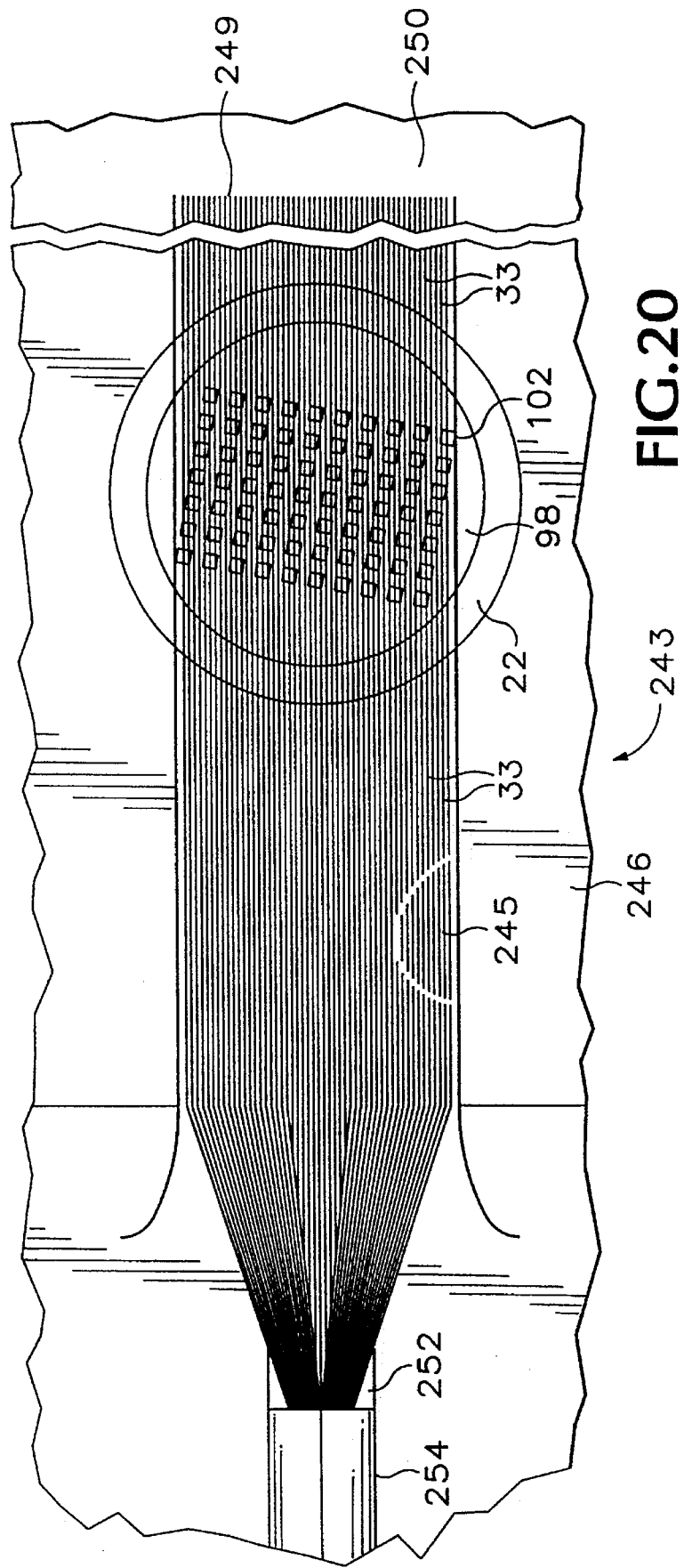

METHOD OF MAKING PERCUTANEOUS CONNECTOR FOR MULTI-CONDUCTOR ELECTRICAL CABLES

BACKGROUND OF THE INVENTION

The present invention relates to biologically implantable percutaneous connectors, and in particular, such connectors for use with cables including many small electrical conductors.

Recent research has made it desirable to carry electrical signals to or from nervous tissue using many individual electrical conductors, each of which may lead within a person's or animal's body to one or more electrodes associated with living cells, so that artificially produced electrical neural stimulation signals may be carried to such nervous tissue. It is desired, at least for experimental purposes, to use such artificial stimulation of nervous tissue to restore lost hearing or sight. In other instances, it may be possible to use such electrical stimulation to control voluntary muscles.

Electrical conductors may also be used to control or provide power to devices such as pumps used to deliver drugs to specific internal organs.

It is important, however, in establishing electrical connections into the interior of a living person or animal, to minimize the risk of infection by microbes entering the body at the site of a percutaneous conduit. It is therefore desirable to use as few percutaneous conduits as possible, and to connect as many as possible of a required number of electrical conductors through each percutaneous conduit.

At times, particularly in conducting experimental development of electronic devices for stimulating nervous tissue, it will be necessary to disconnect external electrical devices from implanted cables, although it is desirable to leave the implanted cables and electrodes in place in order to avoid the trauma of their removal and replacement.

Pin-and-socket connectors used in the past for applications similar to those described above are undesirably large and difficult to use where more than a very few conductors are concerned, since they require a considerable amount of space and present a likelihood of excessive trauma to an animal or person fitted with such a connector. Such pin-and-socket connectors also present the likelihood of accumulation of harmful microbes on the surfaces of their pins and within the socket cavities.

Other problems with pin and socket connectors are that accidental disconnection of such connectors presents the risk of damage to the pins or sockets, and the forces needed ordinarily for connecting and disconnecting such connectors may tend to disturb implanted connector parts, or else limit undesirably the number of conductors which can be connected through such a connector without such risk.

Accordingly, it is desired to provide a percutaneous connector by which external cables can be disconnected from and reconnected easily to implanted electrical cables, particularly ones which include a large number of small electrical conductors.

The success of a prosthetic device for controlling motor movements or for providing artificial vision or hearing in humans will be in part contingent upon the device's size. Practicality of any device of this type necessitates that components be miniaturized such that the wearer can be mobile and unencumbered by large devices or electrical leads.

The wearer of the device must undergo surgery to have internal electrical leads attached to the appropriate nervous tissue. It is highly advantageous to be able to implant as many internal leads as necessary in one surgical operation thereby obviating the need to perform surgery again. In turn, these electrical leads will be affixed to the percutaneous connector base usually attached to the wearer's skull.

An implantable percutaneous connector, to be practical, must be durable. An implantable percutaneous connector will be subjected to many physical manipulations during the course of its use. During testing of neuroprosthetic devices the percutaneous connectors are subjected to multiple cycles of mating and unmating. Implantable percutaneous connectors made of ceramic material, calcium hydroxy-apatite, or vitreous carbon run the risk of being easily broken or chipped during implantation or by accidental post implantation contact. Titanium, on the other hand, is very durable but will have an impact on the overall size of the connector.

Corbett, III, et al. U.S. Pat. No. 5,274,917 discloses a small connector for multi-conductor cables, but the connector disclosed is not adapted for implantation in living tissue.

In the use of percutaneous connectors it is very desirable to restore and maintain the integrity of the skin surrounding the connectors as a barrier to entry of microbes into the body of an animal or person. It is therefore desirable that tissue surrounding a percutaneous connector should readily attach itself to the surface of an implanted percutaneous connector. While the desirability of such biointegration is well known, it has been difficult to accomplish in the past. Various surfaces have been used in the past in attempts to promote biointegration with greater or lesser degrees of success. For example, Aoki U.S. Pat. Nos. 5,035,711 and 5,026,397 disclose a percutaneous connector having a body formed of sintered hydroxyapatite ceramic material in order to promote biointegration.

Byers U.S. Pat. No. 4,645,504 also discloses a percutaneous conduit fashioned of calcium hydroxyapatite presenting a porous surface intended to promote biological integration as a seal against intrusion of pathogens percutaneously.

Owens U.S. Pat. No. 4,025,964 discloses a percutaneous connector in which a radially extending base flange has holes through which tissue can grow beneath the skin to hold the connector in place, while the separable parts of the connector are held together by magnetic attraction to provide electrical connection through metal contacts.

Parsons U.S. Pat. No. 3,995,644 discloses a percutaneous connector having a body of vitreous carbon in which a neck portion of a reduced diameter is utilized to promote healing of skin around the surface of the connector where it projects through the skin. Within the body of the percutaneous connector a dielectric epoxy adhesive is used to seal the penetration of electrical conductors through the connector body into the tissue of a living organism.

What is desired still, however, is a small percutaneous connector providing the capacity for a relatively large number of electrical conductors, which is easily disconnected and reconnected, and yet which also minimizes the risk of accumulation of contaminants on connector surfaces regardless of whether or not the connector is connected.

SUMMARY OF THE INVENTION

The present invention provides an improved implantable percutaneous connector for use in connecting and disconnecting a large number of conductors included in one or more implanted electrical cables with a similar number of conductors of a cable located externally of a living person or animal. In such a connector contacts are provided in corresponding arrays in an implanted half and a removable outer half of the connector, and an anisotropically conductive connector layer is provided between the arrays to interconnect the contacts in one of the arrays with their respective counterparts in the array located in the other part of the connector. This structure enables the connector to include many more conductor connections in a particular size connector than has been possible previously.

A contact block is included in at least the implantable half of the percutaneous connector according to the invention and includes a group of electrically conductive rods held securely in a matrix of dielectric material, with a mating surface of the contact block including an end of each rod of the group as one of the contacts of that array. An opposite terminal face of the contact block includes a terminal end of each of the electrically conductive rods, and each conductor of a multi-conductor implantable cable is connected electrically to a respective one of the terminal ends. A suitable sealant covers the connections of the conductors to the terminal ends, to prevent body fluids from coming into contact with surfaces of the conductors or the terminal ends of the rods.

The invention also provides a cable system including a pair of cables. interconnected through such a percutaneous connector.

Additionally, the invention provides a method for making a percutaneous connector, including the steps of supporting an array of electrically conductive rods extending through respective holes defined in one or more templates while securely embedding and sealing the rods in a dielectric material in such an arrangement. Thereafter, the dielectric material is cured, sintered, or otherwise appropriately stabilized to adhere sealingly to the rods as a matrix surrounding the rods, and the rods and the dielectric material are then shaped to define a mating face and a terminal face each including an array of contacts in the form of mating end surfaces or terminal end surfaces of the several rods. The mating face contacts can be electrically connected to a corresponding array of contacts placed in proper alignment with the terminal ends of the rods.

In one embodiment of the invention the exposed surfaces of the implantable half of the percutaneous connector according to the present invention are preferably coated with a thin layer of a glass having a composition known to promote adhesion and integral growth of bone and soft tissue, known by its trademark BIOGLASS, to promote biointegration with the implanted portions of the connector.

BRIEF DESCRIPTION OF THE DRAWINGS

FIG. 1 is an isometric view of a multi-conductor percutaneous connector suitable for mounting on bone, which is an embodiment of the present invention.

FIG. 2 is an exploded view showing the two connectable halves of the connector shown in FIG. 1 disconnected from each other, together with a sheet of anisotropic electrical connecting material for use between the connector halves.

FIG. 3 is an exploded view of the percutaneous connector shown in FIG. 1, without the fasteners used to assemble the various parts.

FIG. 5 is an isometric view of a contact block useful as a part of a connector similar to that shown in FIGS. 1–4.

FIG. 6 is an exploded view showing some of the components of the contact block shown in FIG. 5.

FIG. 7 is a section view taken along line 7—7 of FIG. 5, showing such a contact block at a first stage during the process of assembly thereof.

FIG. 8 is a view similar to that of FIG. 7 showing a subsequent stage of assembly of such a contact block.

FIG. 9 is a view similar to that of FIG. 7, showing such a contact block upon completion of its assembly and preparation.

FIG. 11 is a section view, taken along line 11—11, of the fixture and collars shown in FIG. 10 assembled together with conductive rods, in a first step of manufacture of a pair of contact blocks in accordance with one method embodying the present invention.

FIG. 12 is a view similar to that of FIG. 11, showing a subsequent stage of preparation of the contact blocks.

FIG. 13 is a section view similar to that of FIG. 11, showing the completed contact blocks prepared in accordance with the method depicted in FIGS. 10–12.

FIG. 20 is a top plan view, at an enlarged scale, of a portion of the array of conductors shown in FIG. 19 together with the contact block and a part of the fixture used to fasten the conductors to it.

DETAILED DESCRIPTION OF THE PREFERRED EMBODIMENTS

Figure 23:
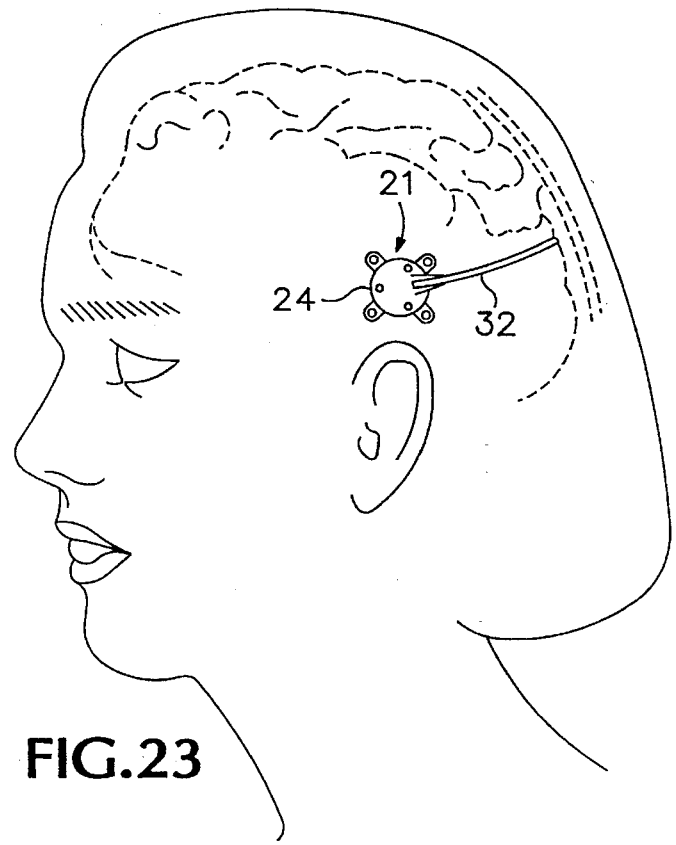
FIG. 23 is view of a person's head in which a percutaneous connector according to the invention has been implanted.

Referring now to the drawings which form a part of the disclosure herein, in FIGS. 1–3, a percutaneous connector 20, intended principally for attachment to bone tissue located close to the surface of the skin of a living mammal, includes an implanted connector half 21 having a lower contact block 22 mounted upon a base 24 adapted to be fastened securely to a surface of bone tissue, initially through the use of fasteners such as screws (not shown) extending through holes 26 defined in arms 28 extending radially from the base 24. A sealing layer 30 is located between the lower contact block 22 and the base 24, and a biologically implantable multi-conductor electrical cable 32 extends away from the base 24 along a ramp 34 extending radially from the base 24 between a pair of the arms 28. The cable 32 may be attached securely to the distal end of the ramp 34 by a suture 36. Such an implanted connector half 21 may be attached to such bone tissue so that the connector half 21 extends percutaneously, with an outer skin surface being located with respect to the height of the implanted connector half 21 as indicated by the broken lines 23 in FIG. 1, for example, in a location on a person's skull, as shown in FIG. 23. The percutaneous connector 20 shown in FIGS. 1–4 and 20 may be attached to a skull of a human, with the conductors 33 of the cable 32 extending to corresponding implanted electrodes intended to transmit electrical impulses to neural tissue, and to receive electrical signals from surrounding neural tissue. The cable 32 extends subcutaneously away from the connector 20 to a separately prepared opening through the bone tissue giving access to the desired portion of the brain where such electrodes are implanted.

An upper, or outer, half 40 of the percutaneous connector is removably connected to the implanted connector half 21 to interconnect the several conductors of a cable 42 to the several conductors of the cable 32, through a layer 44 of elastomeric anisotropically conductive connector material, located between the upper half 40 of the connector and the implanted half 21.

The upper half 40 is removably connected with the implanted half 21 by fasteners such as countersunk socket-headed screws 46 extending through bores 48 defined in the upper half 40 and holes 50 defined through the anisotropically conductive connector layer 44, into threaded bores 52 defined in the lower contact block 22. The screws 46 thus attach the upper half 40 to the implanted half 21 of the connector with sufficient force to provide reliable electrical interconnection through the layer 44, while they also keep the upper half properly aligned with the implanted connector half 21. Tension in the screws 46 also produces sufficient pressure between the upper half 40 and the implanted half 21 to prevent moisture from penetrating between the layer 44 and either the upper half 40, or the implanted half 21, of the connector 20.

Similarly, fasteners such as countersunk socket-headed screws 54 extend through respective bores 56 defined by the lower contact block 22, extending through the lower contact block 22 and the sealing layer 30 into respective threaded bores 58 in the base 24. The screws 54 are preferably tightened enough to compress the sealing layer 30 slightly, thus helping to exclude moisture such as body fluids from the space between the lower contact block 22 and the base 24.

Referring in particular to FIG. 3, the detachable outer or upper half 40 of the connector 20 includes a housing 60, which receives an upper contact block 62 within a cavity 64 defined within its interior. A cap 66 is attached to the housing 60 by a pair of small screws 68 which extend through bores 70 defined through the cap 66 into threaded bores 72 defined in the housing 60, thus retaining the cap 66 properly located and oriented with respect to the housing 60 and the upper contact block 62.

A lower portion of the upper contact block 62 fits closely within an opening 74 which may be of a generally rectangular shape, while a generally circular upper part 75 of the upper contact block 62 acts as a flange to rest upon a shelf 76 defined within the cavity 64 and surrounding the opening 74. An opening 78, through which the cable 42 extends, is defined jointly by the cap 66 and housing 60.

Figure 4:
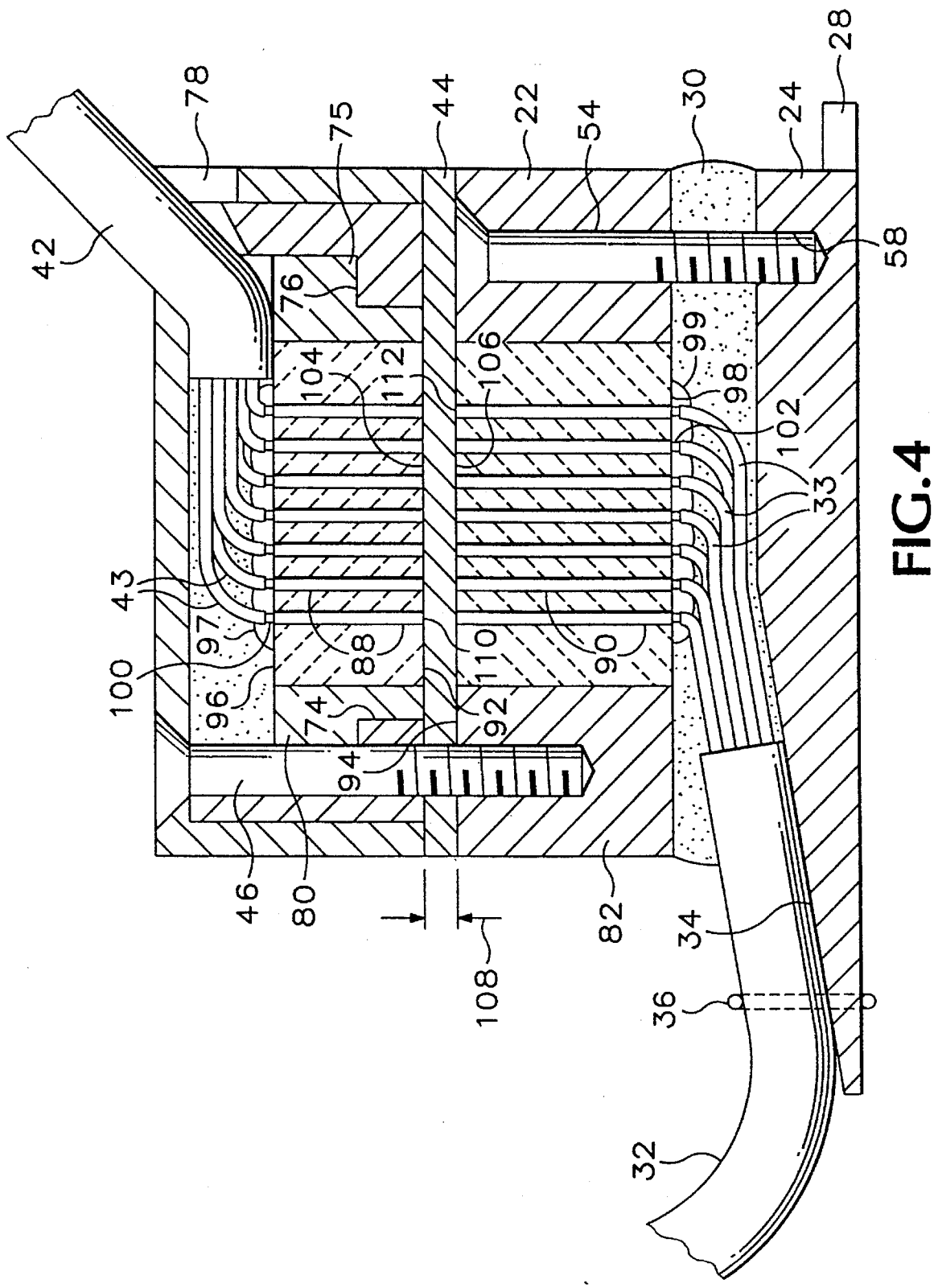
FIG. 4 is a section view of the percutaneous connector shown in FIG. 1, taken along line 4—4 at an enlarged scale.
Figure 10:
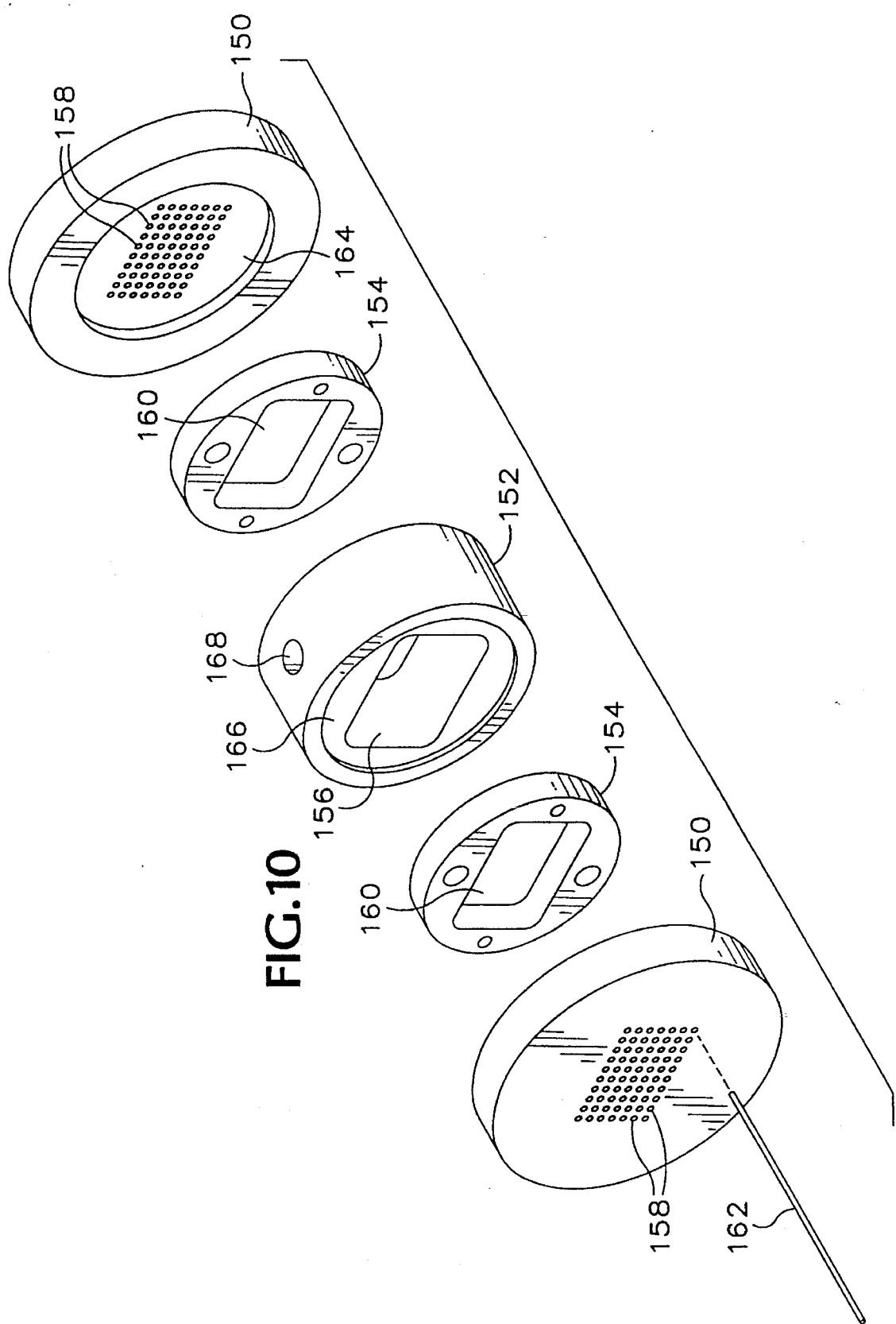
FIG. 10 is an exploded view of a pair of collar members aligned with each other and a three-part fixture for assembly of such a pair of contact blocks for use in percutaneous electrical connectors according to the present invention.

The upper and lower contact blocks 62 and 22 each include a respective collar member 80, 82, within which is located a respective matrix 84, 86 locating and securely holding corresponding arrays of conductive rods 88, 90 which extend entirely through each contact block 22 or 62, from a respective mating face 92, 94 to a respective terminal face 96, 98 (FIG. 4). The mating faces 92, 94 are essentially planar, in this embodiment of the invention, so that the mating surface is relatively easily kept sterile.

Each of the several conductors 43 of the cable 42 is connected electrically with a terminal end 100 of a respective one of the electrically conductive rods 88, and each of the respective conductors 33 of the cable 32 is connected to a respective terminal end 102 of a respective one of the electrically conductive rods 90. The form of such electrical connection may depend upon the size of the several conductors and of the electrically conductive rods 88, 90. For example, with very small conductors 33 and 43 and correspondingly small electrically conductive rods 88 and 90 of gold, pressure-formed wire bond connections may be accomplished, and the rods 88 and 90 may be arranged in perpendicular rows and files with center-to-center spacing in the row or file as small as 0.635 mm (0,025 inch), using gold rods 88, 90 whose diameter is equal to half of the center-to-center spacing. An array of as many as 70 mating ends, to receive an equal number of individual conductors 33 or 43 can thus be included in a single percutaneous connector 20 that is 12.5 mm (0.5 inch) in diameter.

After connection of the cables 32, 42, respectively, to the terminal faces 96, 98, a quantity of a suitable curable dielectric material 97, 99 such as an epoxy adhesive is applied to seal the terminal faces 96, 98 and to provide a stronger mechanical connection of the several conductors respectively to the terminal face 96 or 98. Additional sealant material, preferably of an elastomeric nature such as a UV curable or RTV implantable silicone, may be cast or molded over the epoxy adhesive or other dielectric material 97, 99 to form the sealing layer 30 between the terminal face 98 and the base 24. For example, a biologically implantable elastomeric silicone material well known as Dow-Corning MDX4-4210 is suitable. The epoxy sealant dielectric material 97, 99 covers the portions of the various conductors 33, 43 from which individual jackets of insulation have been removed in order to connect the conductors to the terminal ends 100, 102 of the rods 88, 90. Thus, the sealing dielectric material electrically insulates each of the various conductors 33, 43 of the cables 32, 42 from one another and also protects the terminal faces of the contact blocks 22, 62 from intrusion of corrosive or electrolytic fluids to which the connector 20 might be exposed during use.

The sealing layer 30 is made by molding appropriate material in place on the bottom side of the conductors of the cable 32 after electrical connection of the individual conductors of the cable 32 to the lower contact block 22 as will be explained in greater detail below. The sealing layer 30 is preferably of an elastic silicone material. In order to cause the sealing layer 30 to adhere, a primer in the form of a low-viscosity liquid is brushed onto the clean surfaces of the dielectric material 99 and of the contact block 22 and the cable 32, where it is allowed to dry as a thin film. Thereafter, a mold (not shown) whose interior surfaces are treated with an appropriate release agent is placed over the bottom side of the contact block 22 to form the sealing layer 30 to mate against the base 24 and to have a regular cylindrical side surface 31 and filled with the silicone material of the sealing layer 30. Once the sealing layer 30 is cured the mold is removed leaving the sealing layer 30 adhered to the contact block 22.

Preferred materials for the primer are silane compositions available from United Chemical Technologies, Inc., of Bristol, Pennsylvania, as its CAS product numbers M8450 and A0700, either of which is suitable for use as received from the manufacturer. The CAS M8450 material is a 3-mercaptopropylmethyldimethoxysilane, whose molecular formula is $C_6H_{18}O_2SSi$. The CAS A0700 material is n-(2-aminoethyl)-3-aminopropylmethyldimethoxysilane whose molecular formula is $C_8H_{22}N_2O_3Si$.

When the connector 20 is assembled as shown in FIG. 1, the contact blocks 22 and 62 are aligned with each other, aligning the arrays of conductive rods 88, 90 with each other. A mating end 110 of each conductive rod 88 of the upper contact block is thus located in direct alignment with a mating end 112 of an electrically conductive rod 90 of the lower contact block 22, with the layer 44 of elastomeric anisotropic connector material located between corresponding ones of the mating ends 110 and the mating ends 112 and electrically interconnecting the corresponding ones of the conductive rods 88 and 90 with each other, thus accomplishing in a small area a large number of electrical interconnections between the individual conductors 33, 43 of the cables 32 and 42.

Following disconnection of the cable 42 from the cable 32, by removal of the upper half 40 of the connector 20 from the lower, or implanted, half 21, the anisotropic connector material of the layer 44 may, preferably, be replaced in reconnecting the connector halves.

The material of the layer 44 may be, for example, a curable anisotropically conductive elastomer such as one available from A.I. Technology, Inc., of Princeton, N.J., or from Zymet, Inc. of Hanover, N.J., or anisotropically conductive elastomeric sheet material which is conductive in a direction normal to the major faces of such sheet material, which is available, for example, from Shin-Etsu Polymer of Union City, Calif. as its GB Matrix connector material or its MAF-Connector. Such sheet material consists of gold-plated or nickel-boron plated brass filament fibers embedded at regular spacings within a thin sheet of elastomeric dielectric material such as a silicone rubber. The metal fibers are oriented parallel with one another and generally normal to the major plane of the sheet of material, and protrude several microns above the parallel major surfaces 104, 106 of the anisotropically conductive material to contact and interconnect opposed conductors aligned with each other on opposite sides of the connector layer 44. For example, such a connector sheet may have a thickness 108 of 0.3 mm (0.008 in), and may include metal filaments whose diameters are approximately 0.04 mm (0.001 inch) in diameter distributed fairly evenly, to provide approximately 40 filaments per square millimeter (25,800 filaments per square inch) passing through the entire thickness of the connector sheet.

In order for the connector 20 to cause a minimum of irritation to the surrounding tissue, at least the base 24 and the collar 82 of the lower contact block 22 are of a biologically inert material, such as titanium, and the surfaces of those elements which are exposed to contact with bone or soft tissue where the connector 20 is implanted are coated, preferably, with a thin layer of glass having a specific composition known by its trademark BIOGLASS. Such glass is applied in a coating having a thickness of 50 microns to 150 microns total thickness in order to prevent downgrowth of epithelial tissues and to bond with connective tissue. A method for applying such a coating has been described by West, who teaches use of a boric acid ground coat to which the bioglass coating adheres. The bioglass material may also be applied by a plasma spraying process which is well known, and which may require more than one layer to achieve the desired thickness.

Referring next to FIGS. 5–10, one method of preparing a contact block such as the lower contact block 22 or the upper contact block 62 is shown in connection with a similar contact block 120. The contact block 120 includes a matrix 122 of dielectric material surrounding a plurality of electrically conductive rods 124 arranged and held in a predetermined array by a template 126 located within a collar 128. An opening 130 is defined by the collar 128, and the template 126 fits closely within the opening 128, supported on an inwardly-projecting shelf 132 which establishes the proper position of the template 126 between opposite faces 134, 136 of the collar member 128.

The template 126 may be made of a suitable dielectric material such as a ceramic, and defines an array of bores 138 which are preferably parallel with one another and extend directly through the template 126 so as to be oriented normal to the parallel faces 134, 136 of the collar 128 when the template 126 is properly located within the opening 130.

The contact block 120 is prepared by placing a respective electrically conductive rod 124 into each of the several bores 138, which are preferably of a size to receive the rods 124 snugly but slidably. Once the rods 124 have been placed within the bores 138 the template 126 is placed within the opening 130 as shown in FIG. 7, where it is located resting properly against the shelf 132. Thereafter, a quantity of a suitable curable dielectric adhesive sealant material 140, preferably in a viscous liquid form, is inserted to fill the opening 130 and to extend a slight distance outward beyond the respective face 134 or 136 of the collar 128. A suitable material for this use is a curable epoxy dielectric material such as Epo-Tek®301, available from Epoxy Technology, Inc. of Billerica, Mass., as a two-part epoxy adhesive system. The material 140 is then cured by appropriate treatment in accordance with the manufacturer's recommendations.

Another material 140 suitable for use as a matrix 122 is a thermosetting silicone resin which cures to a rigid state, such as that available from NuSil Technology of Carpenteria, Calif., as its product number CF-4721 Thermosetting Silicone Resin. Prior to curing it is a liquid, but with use of 2% by weight of Di-tertbutyl peroxide as a catalyst, and curing for two hours at 177° C. (350° F.) after degassing, it cures to a rigid form and has satisfactory dielectric properties.

Once the sealant adhesive material 140 has been cured to securely hold the conductive rods 124 and the template 126 in place within the opening 130, the rods 124 and the surrounding cured adhesive sealant 140 are ground and polished with abrasives to form the completed contact block as shown in FIGS. 5 and 9, in which opposite ends of the rods 124 are located on opposite sides of the collar 128 in a predetermined arrangement. A planar surface of a mating end 142 of each electrically conductive rod 124 is surrounded by a surface of the sealant adhesive 140 as the matrix 122, and the surface of a first or mating face 134 of the contact block 120, the matrix 122 and the included mating ends 142 are all smooth and coplanar.

On the parallel opposite side of the contact block, the rods 124 and the adhesive sealant material 140 are also made smooth and coplanar with the face 136 of the collar 120 as a terminal face of the contact block 120, in which a respective terminal end 144 of each rod 124 is exposed, surrounded by a surface of the matrix 122 of sealant adhesive material 140.

Individual conductors, such as the conductors 33 of the cable such as the cable 32 shown in FIGS. 1–4, are separated and insulation is removed from an appropriate length of each of such conductors to permit the conductors individually to be wire bonded or welded to the terminal ends 144 of the respective conductive rods 124 to interconnect them electrically and mechanically. Once such connections have been made to the terminal face 136 of the contact block 120, an additional amount of an adhesive sealant, which may be the same as the material 140 used to secure the conductive rods 124 in place, is preferably applied as the dielectric material 97, 99 of the connector 20 shown in FIGS. 1–4, to seal these connections at the terminal face of the contact block. Either with or without such a sealant dielectric layer, a biocompatible adhesive elastomer such as Dow Corning MDX4-4210 is applied to and cured on the terminal face of the contact block as a sealing layer such as the sealing layer 30 of the connector 20 shown in FIGS. 1–4.

In a slightly different method for preparing the contact blocks such as the lower contact block 22 and upper contact block 62, as shown in FIGS. 10, 11, 12 and 13, a fixture 148 includes a pair of opposite end members 150 and a central member 152 that are aligned with one another. The fixture 148 is used to hold a pair of collars 154 similar to the collar 128 described above, although they need not include the shelf 132 of the collar 128.

The collars 154 are placed between the members 150, 152 of the fixture, aligned with the cavity 156 defined within the central member 152. An array of parallel bores 158 is provided in each of the end members 150, and the arrays are aligned with each other, with the cavity 156, and with respective openings 160 defined by the collars 154, and the entire assembly is held tightly in this arrangement by a suitable clamp. While the fixture 148 and the collars 154 are thus held securely together, electrically conductive rods 162 are placed through the bores 158 of one of the end members 150 and thence inserted through the openings 160, the cavity 156, and through the corresponding bores 158 in the opposite one of the end members 150 of the fixture to form the arrangement shown in FIG. 11. With all of the bores 158 occupied by corresponding rods 162, with the collars 154 continuing to be held tightly within the fixture, and with each collar 154 held between one of the parallel faces 166 of the central member 152 and the inner face 164 of the respective end member 150, a quantity of a dielectric potting material 170 such as a medical grade two-part epoxy system available from Epoxy Technology of Billerica, Mass. under the trade name Epotek 301, is injected within the cavity 156 through the conduit 168, to fill all the available space among the rods 162 within the cavity 156 and the openings 160. Such potting material 170 should be introduced carefully, so as not to exert excessive force on the rods 162 and thus bend them.

The potting material 170 is then cured, leaving the fixture and the collars 154 united as a monolithic assembly including the parallel electrically conductive rods 162 extending as an array through each of the openings 160 defined within the collars 154.

Thereafter, the central member 152 and the portions of the rods 162 extending through the cavity 156 defined by the central member 152 are divided into two parts, as by sawing, and the portions of the rods 162 extending beyond either side of each of the collars 154 are machined away, and then smoothed as by use of abrasives and lapidary methods, to produce the parallel mating face 172 and terminal face 174 of each of a pair of similar contact blocks 176 whose mating faces 172 thus include corresponding mating ends 178 each of which was once a part of the same one of the electrically conductive rods 162.

The end pieces 150 and central member 152 of the fixture may be manufactured of a suitable plastics material, such as a polycarbonate, by use of conventional injection molding techniques. The bores 158 through each of the end members 150 may, depending upon the size, be made as a part of the molding process or may be defined later by use of computer-controlled laser machining techniques.

Instead of using epoxy potting material 170, in another embodiment of the invention the matrix of material surrounding the rods 162 within the openings 160 may be formed of a ceramic material, or of a glass frit densified by exposure to a suitably high temperature and pressure. When using such materials the fixture 148 must be made of material capable of withstanding the temperature used to sinter, fire, or fuse the material of the matrix. For example, the fixture 148 could be of aluminum, since it can be cast and machined readily and is not too expensive.

Although conductive rods 162 are preferred, because of the heating and cooling involved, the rods 162 in such a matrix may be of an alloy having a thermal coefficient of expansion similar to that of glass, such as a nickel-iron alloy including about 29% Ni, 17% Co, 0.3% Mn and the balance being iron, in order to have similar thermal coefficients of expansion, keeping in mind that the resulting greater tendency for contact surfaces to oxidize may make it necessary to gold plate the mating end surfaces 178 to prevent corrosion and maintain low contact resistance.

Figure 14:
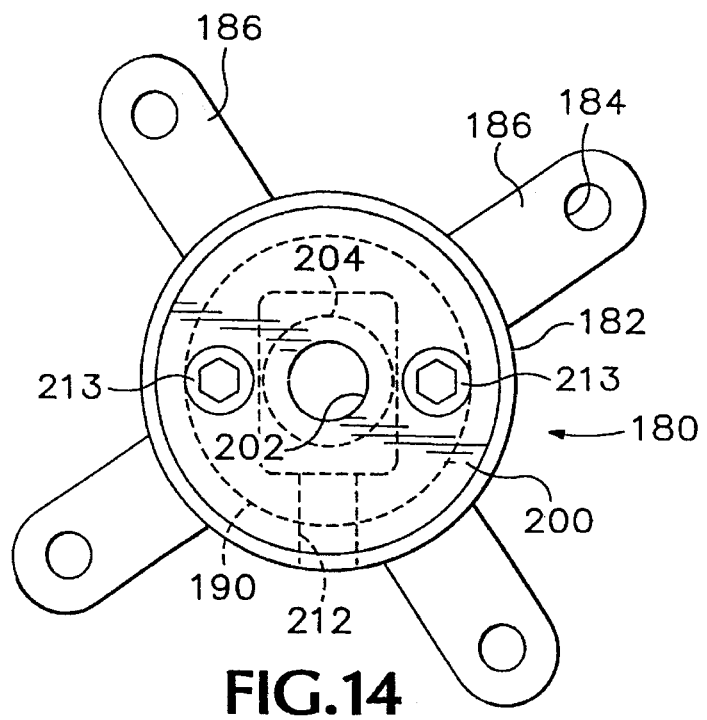
FIG. 14 is a top plan view of a connector embodying the present invention and intended for implantation including attachment to bone tissue located close to the surface of skin tissue.
Figure 15:
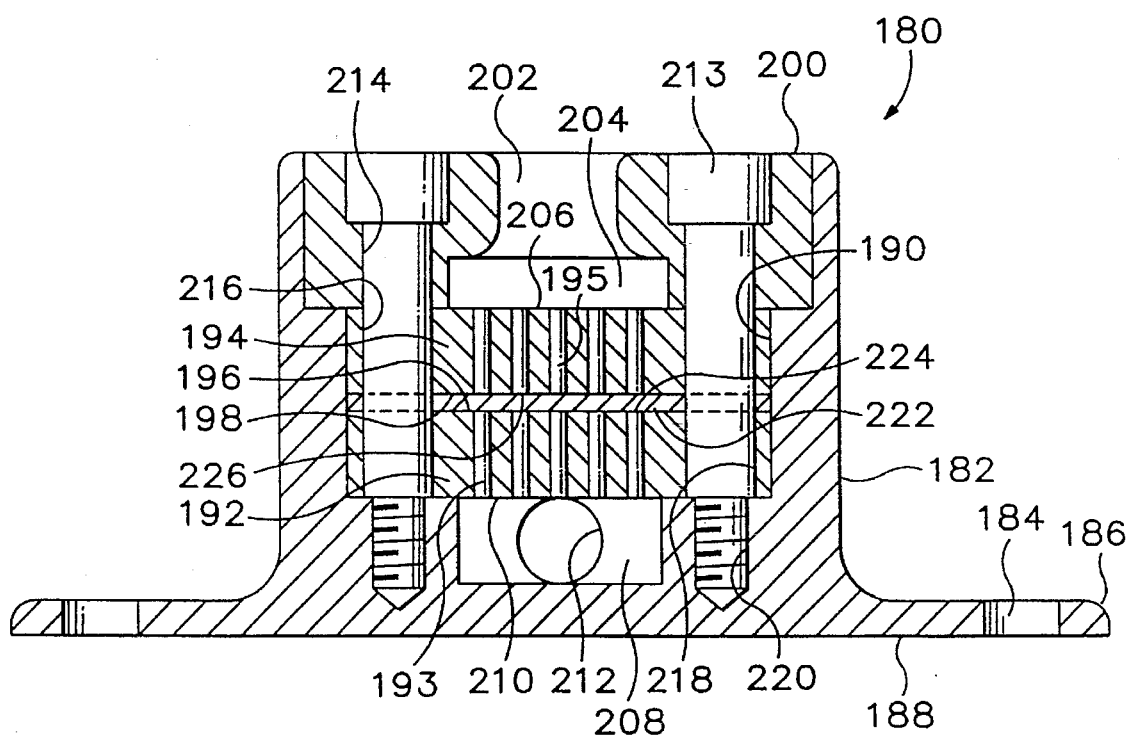
FIG. 15 is a sectional view of the connector shown in FIG. 14, taken along line 15—15.

As shown in FIGS. 14 and 15, a percutaneous connector 180 includes a generally cylindrical housing 182 which can be attached to a surface of bone tissue in a living body by the use of appropriate screws extending through holes 184 in arms 186 extending radially from the base end 188 of the housing 182. As with the connector 20, the housing 182 is preferably coated with an osseointegration- and biointegration-promoting material such as BIOGLASS.

A cylindrical cavity 190 is defined within the housing 182 and a pair of corresponding contact blocks, a lower contact block 192 including conductive rods 193 in a matrix of dielectric material and an upper contact block 194 including similar rods 195, fit snugly within the cavity 190. Both of the contact blocks 192 and 194 may be generally similar to the contact blocks 120 and 176, for example, and each has a respective mating face 196, 198 including an array of mating ends 224, 226 similar to the mating ends 178 of the contact block 176. A cover 200 defines a cable port 202 and a cavity 204 beneath the cable port to provide room for connection of the several conductors of a cable to the terminal face 206 of the upper contact block 194, in the same way in which the conductors 43 are attached to the terminal ends 100 of the rods 88 of the contact block 62 (FIG. 4).

A cavity 208, defined in the housing 182 beneath the cavity 190, is open to expose a terminal face 210 of the lower contact block 192. A cable port 212 communicates with the cavity 208, extending to the exterior of the housing 182 as a conduit for an implantable cable having connectors individually connected electrically and mechanically to respective terminal ends of conductive rods 193 incorporated in the lower contact block 192.

A pair of fasteners 213, which may preferably be socket headed body-fitted screws, extend through respective fitted bores 214 in the cover 200, fitted bores 216 in the upper contact block 194, and fitted bores 218 in the lower contact block 192, and are engaged in threaded bores 220 defined in the housing 182. When the screws 213 are tightened, they squeeze the contact blocks 192 and 194 together, urging the mating faces 196 and 198 against a layer 222 of anisotropic conductive elastomeric connector material located between them to interconnect the respective mating ends 224, 226 of the conductive rods 193 and 195 of the upper and lower contact blocks 192 and 194 with their counterparts, thus interconnecting the corresponding conductors of the cables.

Figure 16:
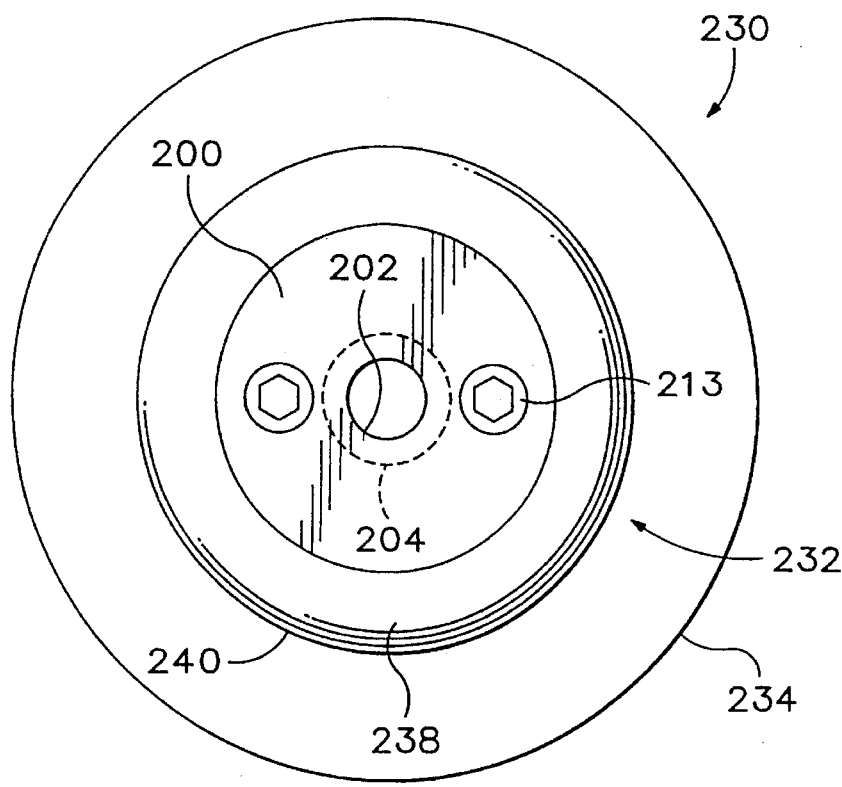
FIG. 16 is a top plan view of a connector which is another embodiment of the present invention and which is particularly adapted for implantation in soft tissue.
Figure 17:
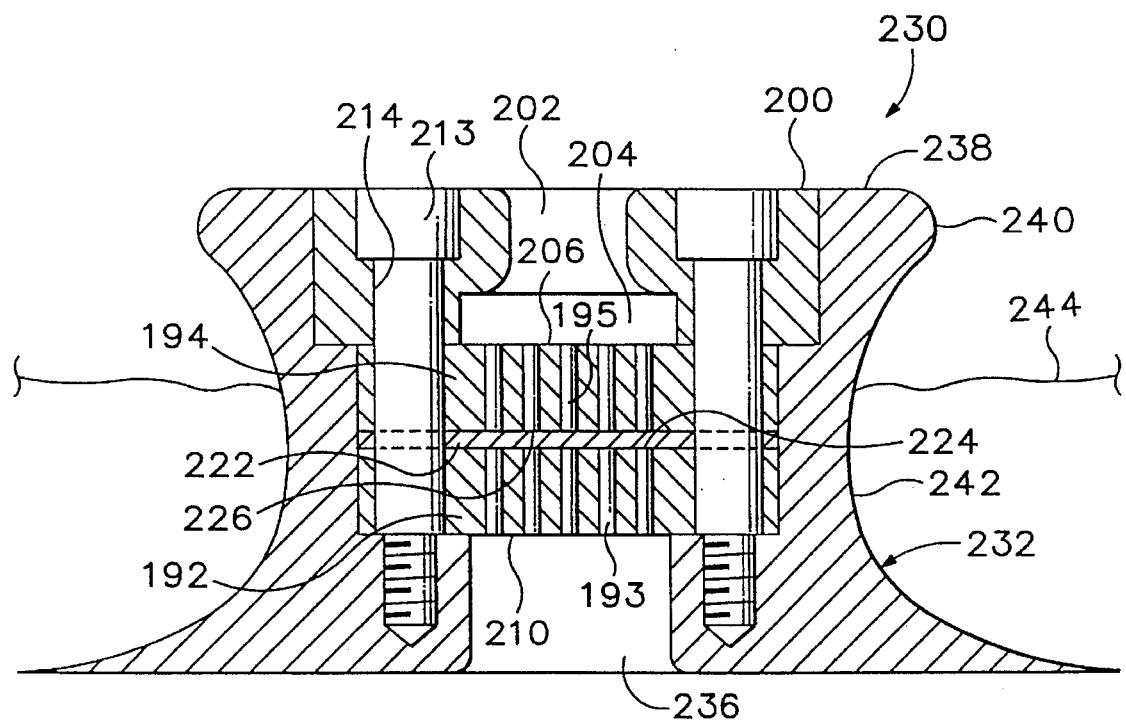
FIG. 17 is a sectional view of the connector shown in FIG. 16, taken along line 17—17.
Figure 18:
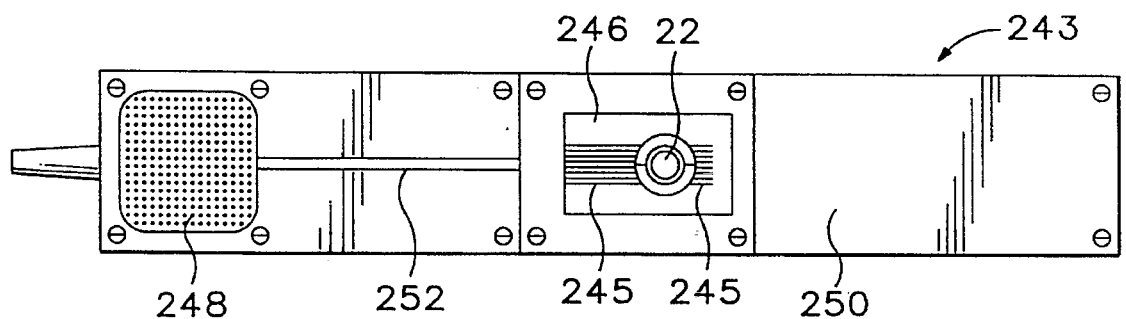
FIG. 18 is a top plan view of a fixture for use in assembling a cable and connecting its conductors to a contact block of a connector according to the present invention.
Figure 19:
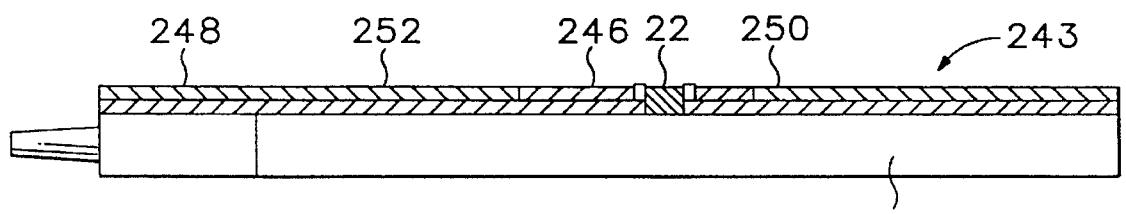
FIG. 19 is a sectional side view of the fixture shown in FIG. 18.
Figure 22:
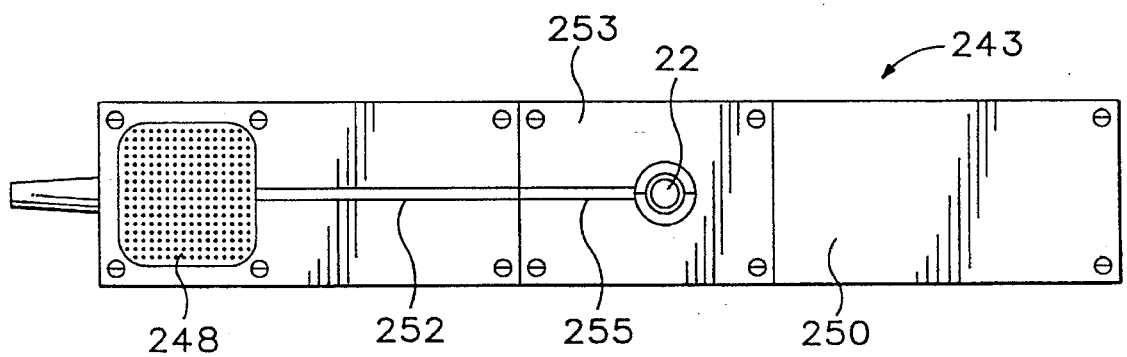
FIG. 22 is a view similar to FIG. 18, with the grooved template replaced by a plate having a single groove.

Referring next to FIGS. 16 and 17, a percutaneous connector 230 is similar in many respects to the connector 180, shown in FIGS. 14 and 15. Like components are designated in FIGS. 16 and 17 by like reference numerals and will not be discussed in detail. The differences are found in the housing 232, which is circular in plan view, with an annular, circular base 234 defining a central cavity 236 which performs as a cable port for a cable (not shown) connected electrically and mechanically with the terminal face 210 of the lower contact block 192. The housing 232 has an enlarged upper, or outer, end 238 with a rounded shoulder 240, and a concavely rounded neck portion 242 is located between the shoulder 240 and the base 234.

The housing 232 may be made, for example, of a biologically implantable metal such as titanium, or of a biologically inert plastic such as a polytetrafluoroethylene (Teflon), vitreous carbon material, or a polycarbonate material. If the housing 232 is of metal it preferably has a coating of BIOGLASS to promote biointegration, that is, adhesion of the surrounding epithelial and other soft tissue, so that the connector 230 will become integrated with the surrounding tissue in order to resist entrance of microbes into the body along the surfaces of the connector housing 232, and in order to resist marsupialization around the connector 230. The percutaneous connector 230 may be surgically implanted to extend through the skin in the vicinity of a paralyzed muscle, for example, with a cable such as the cable 32 extending from the bottom cavity 236 including conductors 33 leading to electrodes implanted appropriately in the paralyzed muscles. For best stability, the connector 230 is implanted with the outer surface 244 of the surrounding skin aligned with the neck 242 of the housing 232, as indicated in FIG. 17.

As shown in FIGS. 18, 19, 20, 21 and 22, a large number of individual conductors 33, together constituting a cable 32, can be attached to respective terminal ends 102 of conductive rods 90 of the terminal face 98 of a contact block 22 of a connector such the connector 20 in an orderly fashion by use of a fixture 243 including an alignment template 246 to arrange and hold the conductors 33 temporarily while they are individually fastened to the appropriate ones of the terminal ends 102. The conductors 33 of a cable 32, for example 64 gold wires, are placed in respective laser-machined grooves 245 in the template 246, which may be a suitable supported polyimide sheet 125 microns (0.006 inch) thick, for example, to align the several individual conductors 33 and keep them in position side-by-side as a single-layer array 247. For example, using gold wires each 25 microns in diameter and covered with a coating of parylene-C four microns in radial thickness (for an overall diameter of 33 microns) as the individual conductors 33, the grooves 245 are preferably parallel, spaced 94 microns apart, center-to-center. Each groove 245 is preferably about 50 microns wide and 75 microns deep.

At one end of the fixture 243 each conductor 33 is individually placed in a required position, as determined, for example, by desired electrode positions for an electrode array 248 where an end of each particular conductor 33 may be retained by use of a vacuum chamber and a perforated matrix to hold an electrode from which a conductor or conductors 33 extend. The particular conductor 33 is then extended along the fixture 243 and placed in an appropriate one of the grooves 245, and is thence extended further along the fixture 243 across the terminal face 98 of the contact block 22 to the far side of the connector contact block 22, with the distal end 249 of the conductor 33 is fastened to the top surface 250 of the fixture 243 by a fast-setting adhesive, such as cyanoacrylic glue. Each conductor 33 is thus held in tension where it extends along the terminal face 98 of the contact block 22, aligned with a particular one of the terminal ends 102 to which the conductor 33 is to be connected. The conductors 33 are thus held very close to one another in the single layer array 247, in positions which are maintained while the conductors 33 are prepared and connected to the terminal ends 102 on the contact block 22 in the configuration shown in FIG. 21.

Between the electrode array 248 and the grooved template 246 a single groove 252, which may be 2.5 mm. (0.1 inch) wide and 1.5 mm. (0.06 inch) deep, defined in the fixture 243 holds a silicone tube 254 slit lengthwise along one side and held upwardly open. Each of the conductors 33 is placed within the tube 254 before its distal end 249 is glued down onto the surface 250 of the fixture 243. Once the conductors 33 have all been placed on the fixture 243 in this manner the support block portion 256 of the fixture 243 is then removed from the bottom of the fixture to provide room for laser delivery microscope lenses, and a laser is used to remove the parylene-C from the exposed upper side of each conductor 33 of the array 247 over a length of 50–75 microns (0,002–0, 003 inch), above the particular one of the terminal ends 102 to which the conductor 33 is to be attached. The contact block 22 is withdrawn downwardly from beneath the array 247 of the conductors 33. The parylene coating is then removed from the bottom side of each of the conductors 33 of the array 247, in locations corresponding to those where the coating had already been removed from the upper side of each conductor 33.

Once the coating of parylene has been removed from the appropriate portions of the conductors 33 by laser scanning from both sides of the array 247, the contact block 22 is replaced into the fixture 22 and aligned with the array of prepared conductors 33, to permit each conductor 33 to be connected electrically and mechanically to the appropriate terminal end 102.

Figure 21:
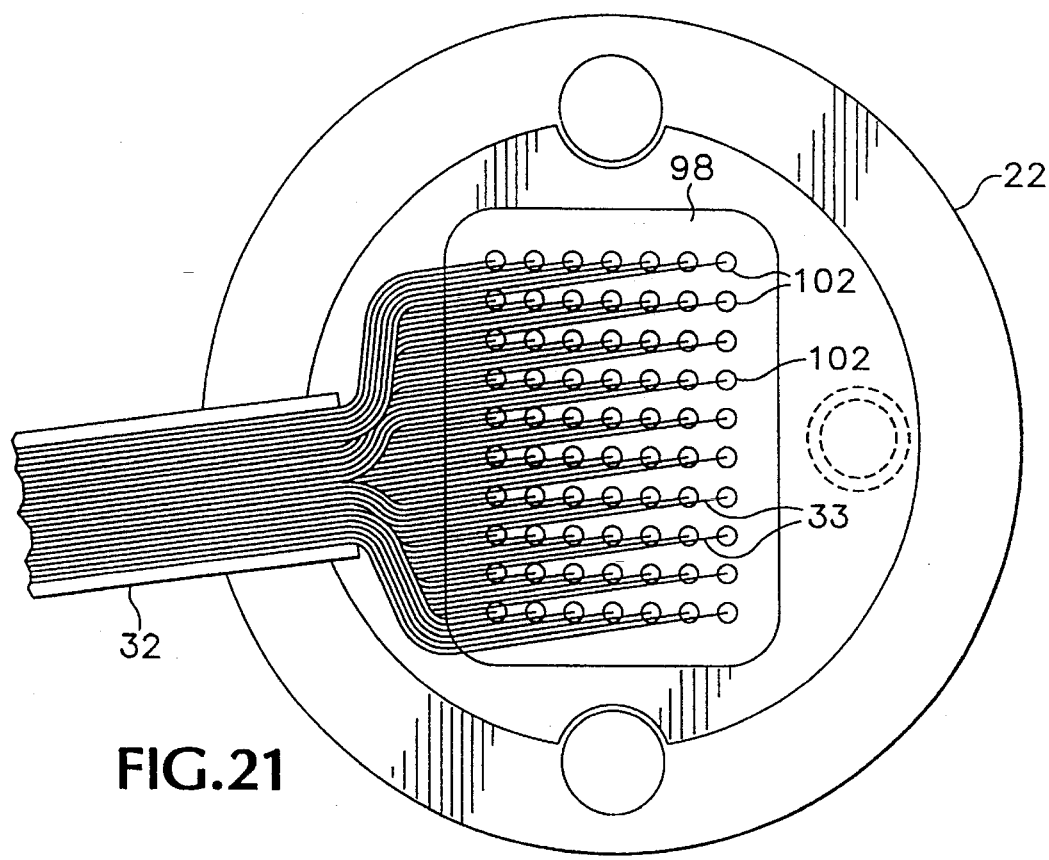
FIG. 21 is a view showing the individual electrical conductors of a cable each connected separately to respective terminal ends of conductive rods on the terminal face of the contact block shown in FIGS. 18–20.

Preferably, attachment of the conductors 33 to the terminal ends 102 is accomplished by sonic bonding techniques similar to those used in connecting integrated circuits to chip carriers. First, the terminal ends 102 of the contact block 22 are heated, as by conducting heat through the conductive rods of a mating contact block (not shown) held in contact with the downwardly exposed face of the contact block 22. Thereafter, a sonic bonder is used to attach the conductors 33 to the respective terminal ends 102. Once the conductors 33 have been sonically bonded to the terminal ends 102 of the contact block 22, the distal portions of the conductors 33 are removed, to leave the finished connector contact block 22 as shown in FIG. 21. Thereafter, the sonic bond joints are reinforced by application of the layer of adhesive 99 (FIG.

4), and eventually the sealing layer 30 will be applied in the manner previously described.

Once the adhesive 99 has been applied and cured, the contact block 22 is raised slightly in the fixture 243, lifting the conductors 33 from their positions in the grooves 245 of the template 246, which is then removed from the fixture 243 and replaced by a plate 253 having a groove 255 similar to the groove 252. A short length of silicone tubing, also slit along one side and held open is placed into the groove 255, and the portions of the conductors 33 located between the end of the tubing 254 and the contact body 22 are gathered into the short length of tubing. Both lengths of the silicone tubing between the electrode array 248 and the contact block 22 are allowed to close around the group of conductors 33 and are filled with a silicone such as the Dow-Corning MDX4-4210 previously mentioned as useful for sealing layer 30. The silicone is then cured, forming a jacket of the cable 32, in which the conductors 33 are embedded, so that the sealing layer 30 can thereafter be applied.

The cable 42 can be connected to the terminal ends 100 of the conductive rods 88 of an upper contact block 62 (FIG. 4) by an analogous procedure.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A method for making a biologically implantable connector for a multi-conductor miniature electrical cable, comprising:

(a) holding a plurality of electrically conductive rods located in respective predetermined positions, with respective portions of said rods extending through a passage defined through a collar;

(b) while said rods are being held in said predetermined positions, embedding at least a respective portion of each rod, located at least partly within said passage, in a matrix of a dielectric material, thereby forming a contact block;

(c) shaping said dielectric material to form a mating face and a terminal face on said contact block, said mating face including a first end of each of said rods surrounded by a surface of said dielectric material of said matrix, and said terminal face including an opposite, terminal end of each said rod surrounded by a surface of said dielectric material of said matrix.

2. The method of claim 1, including, as part of said step of embedding, the steps of placing a perforate support member in a predetermined position in said passage, holding each of said plurality of rods in a respective opening defined in said perforate support member, and placing said dielectric material within said passage and in contact with said support member within said passage so as to hold said respective portions of said rods.

3. The method of claim 2 wherein said perforate support member is of green ceramic material and including the step of sintering said perforate support member in said predetermined position in said passage with each of said rods in place in said respective opening defined in said perforate support member.

4. The method of claim 1 wherein said dielectric material of said matrix is an epoxy resin.

5. The method of claim 1 wherein said step of embedding includes the steps of surrounding a respective portion of each said rod in a quantity of unsintered frit material located at least partly within said passage and heating said collar and said frit material to a predetermined temperature.

6. The method of claim 1 wherein said dielectric material of said matrix is a polymeric resin.

7. The method of claim 6 wherein said resin is a silicone.

8. The method of claim 1 wherein said step of holding said conductive rods includes holding them parallel with each other and spaced apart from one another by a predetermined distance.

9. The method of claim 8 wherein said rods have similar diameters and said predetermined distance is no greater than said diameters.

10. The method of claim 1 wherein said step of forming a mating face and a terminal face includes removing respective portions of said rods and a portion of said insulating material of said matrix to form one of said faces parallel with a planar end face of said collar.

11. A method for making a biologically implantable connector for a multi-conductor miniature electrical cable, comprising:

(a) holding a plurality of electrically conductive rods located in respective predetermined positions, with respective portions of said rods extending through a passage defined through a collar;

(b) while said rods are being held in said predetermined positions, embedding at least a respective portion of each rod, located at least partly within said passage, in a matrix of a dielectric material, thereby forming a contact block, said step of embedding including the steps of placing a perforate support member of green ceramic material in a predetermined position in said passage, holding each of said plurality of rods in a respective opening defined in said perforate support member, placing said dielectric material within said passage and in contact with said support member within said passage so as to hold said respective portions of said rods, and sintering said perforate support member in said predetermined position in said passage with each of said rods in place in said respective opening defined in said perforate support member; and (c) shaping said electric material to form a mating face and a terminal face, said mating face including a first end of each of said rods surrounded by a surface of said dielectric material of said matrix, and said terminal face including an opposite, terminal end of each said rod and including, as part of said step of embedding, the further step of depositing a layer of an adhesive sealant on said perforate support member after sintering said perforate support member, covering said ceramic material and respective portions of said rods, and thereafter shaping said layer of adhesive sealant together with said rods to form said mating face.

12. A method for making a biologically implantable connector for a multi-conductor miniature electrical cable, comprising:

(a) holding a plurality of electrically conductive rods located in respective predetermined positions, with respective portions of said rods extending through a passage defined through a collar;

(b) while said rods are being held in said predetermined positions, embedding at least a respective portion of each rod, located at least partly within said passage, in a matrix of a dielectric material, thereby forming a contact block;

(c) shaping said dielectric material to form a mating face and a terminal face, said mating face including a first end of each of said rods surrounded by a surface of said dielectric material of said matrix, and said terminal face including an opposite, terminal end of each said rod; and (d) depositing a layer of an adhesive sealant over said terminal face of said terminal contact block.

13. A method for making a biologically implantable connector for a multi-conductor miniature electrical cable, comprising:

(a) holding a plurality of electrically conductive rods located in respective predetermined positions, with respective portions of said rods extending through a passage defined through a collar and holding said collar between a pair of end templates aligned with one another, each of said end templates defining an array of bores, said step of holding said plurality of rods including holding said rods parallel with each other at a predetermined spacing from one another with each of said rods having respective portions thereof located within respective ones of said bores;

(b) while said rods are being held in said predetermined positions, embedding at least a respective portion of each rod, located at least partly within said passage, in a matrix of a dielectric material, thereby forming a contact block; and (c) shaping said dielectric material to form a mating face and a terminal face, said mating face including a first end of each of said rods surrounded by a surface of said dielectric material of said matrix, and said terminal face including an opposite, terminal end of each said rod.

14. The method of claim 13, including, as part of said step of embedding, the steps of placing a perforate support member in a predetermined position in said passage, holding each of said plurality of rods in a respective opening defined in said perforate support member, and placing said dielectric material within said passage and in contact with said support member within said passage so as to hold said respective portions of said rods.

15. The method of claim 14 wherein said perforate support member is of green ceramic material and including the step of sintering said perforate support member in said predetermined position in said passage with each of said rods in place in said respective opening defined in said perforate support member.

16. The method of claim 13 wherein said dielectric material of said matrix is an epoxy resin.

17. The method of claim 13 wherein said step of embedding includes the steps of surrounding a respective portion of each said rod in a quantity of unsintered frit material located at least partly within said passage and heating said collar and said frit material to a predetermined temperature.

18. The method of claim 13 wherein said dielectric material of said matrix is a polymeric resin.

19. The method of claim 18 wherein said resin is a silicone.

20. The method of claim 13 wherein said step of holding said conductive rods includes holding them parallel with each other and spaced apart from one another by a predetermined distance.

21. The method of claim 20 wherein said rods have similar diameters and said predetermined distance is no greater than said diameters.

22. The method of claim 13 wherein said step of forming a mating face and a terminal face includes removing respective portions of said rods and a portion of said insulating material of said matrix to form one of said faces parallel with a planar end face of said collar.

23. A method of making a cable system including a biologically implantable connector and an end of an implantable multi-conductor electrical cable, comprising:

(a) holding a plurality of electrically conductive rods in respective predetermined positions, with respective portions of said rods extending through a passage defined through a collar;

(b) while said rods are being held in said predetermined positions, embedding at least a respective portion of each rod, located at least partly within said passage, in a matrix of a dielectric material to form a contact block including said rods;

(c) shaping said contact block to form a mating face and a terminal face, said mating face including a first end of each of said rods surrounded by a surface of said dielectric material and said terminal face including an opposite, terminal end of each said rod surrounded by a surface of said dielectric material; and (d) electrically connecting a plurality of individual conductors of said multi-conductor electrical cable to respective ones of said terminal ends on said terminal face of said contact block.

24. The method of claim 23, including the step of forming a sealing body covering said terminal face and a portion of said cable attached thereto.

25. The method of claim 24, including the steps of providing a base and mounting said block on said base, together with said sealing body, thereby compressing said sealing body between said base and said terminal face of said block.

26. A method of making a cable system including a biologically implantable connector and an end of an implantable multi-conductor electrical cable, comprising:

(a) holding a plurality of electrically conductive rods in respective predetermined positions, with respective portions of said rods extending through a passage defined through a collar;

(b) while said rods are being held in said predetermined positions, embedding at least a respective portion of each rod, located at least partly within said passage, in a matrix of a dielectric material to form a contact block including said rods;

(c) shaping said contact block to form a mating face and a terminal face, said mating face including a first end of each of said rods surrounded by said dielectric material and said terminal face including an opposite, terminal end of each said rod; and (d) electrically connecting a plurality of individual conductors of said multi-conductor electrical cable to respective ones of said terminal ends on said terminal face of said contact block; and (e) covering said terminal face and a portion of each of said conductors connected to a respective terminal end with a layer of an adhesive sealant material.

27. A method of making a cable system including a biologically implantable connector and an end of an implantable multi-conductor electrical cable, comprising:

(a) holding a plurality of electrically conductive rods in respective predetermined positions, with respective portions of said rods extending through a passage defined through a collar;

(b) while said rods are being held in said predetermined positions, embedding at least a respective portion of each rod, located at least partly within said passage, in a matrix of a dielectric material to form a contact block including said rods;

(c) shaping said contact block to form a mating face and a terminal face, said mating face including a first end of each of said rods surrounded by said dielectric material and said terminal face including an opposite, terminal end of each said rod; and (d) electrically connecting a plurality of individual conductors of said multi-conductor electrical cable to respective ones of said terminal ends on said terminal face of said contact block, said step of electrically connecting including:

(i) placing terminal portions of a plurality of said individual conductors parallel with each other in a single-layer array having a top face and a bottom face;

(ii) removing insulation from said individual conductors on said top face of said array;

(iii) removing insulation from said individual conductors on said bottom face of said array;

(iv) thereafter aligning each of said individual conductors of said array with a respective one of said terminal ends while holding said terminal portion thereof in said single-layer array; and (v) mechanically fastening and electrically connecting each of said individual conductors to a respective one of said terminal ends while holding said array in position with respect to said terminal face.

28. The method of claim 27, including using an insulation removal tool to perform said step of placing said terminal portions into said array.

29. The method of claim 27 wherein said step of placing said terminal portions of said individual conductors into said single-layer array includes the step of placing said terminal portions into respective parallel grooves defined in a template.

30. The method of claim 29, including the step of holding said template in a selected position with respect to said terminal face and thereby aligning each of said individual conductors with a respective one of said terminal ends.

31. The method of claim 27, including the step of pressing each of said individual conductors against a respective one of said terminal ends and sonically bonding it thereto.

32. The method of claim 27, including the further step of applying an insulating and sealing coating of an adhesive dielectric material to said terminal face and said individual electrical conductors fastened thereto and thereby providing additional mechanical connection of said cable to said terminal end and insulating said terminal portions of said individual electrical conductors from each other and from ones of said terminal ends other than the respective one to which each is connected electrically.

33. The method of claim 27, including the step of forming a sealing body covering said terminal face and a portion of said cable attached thereto.

34. The method of claim 33, including the steps of providing a base and mounting said block on said base, together with said sealing body, thereby compressing said sealing body between said base and said terminal face of said block.

* * * * *